United States Patent [19]

Middelburg

[11] Plant 4,240

[45] Apr. 11, 1978

[54] CHRYSANTHEMUM

[75] Inventor: Nicolaas Middelburg, 's Gravenzande, Netherlands

[73] Assignee: Middelburg B.V., Netherlands

[21] Appl. No.: 792,487

[22] Filed: Jun. 3, 1977

[51] Int. Cl.[2] ..... A01H 5/00

[52] U.S. Cl. ..... Plt./74

[58] Field of Search ..... Plt./74

*Primary Examiner*—Robert E. Bagwill

*Assistant Examiner*—James R. Feyrer

*Attorney, Agent, or Firm*—Boone, Schatzel, Hamrick & Knudsen

[57] ABSTRACT

A new variety of chrysanthemum plant originating as a sport of Horim (unpatented) characterized by its satiny pure white blooms, vigorous growth, 12 week response, permanence and distinguished from the parent cultivar, Horim, by larger and purer white blooms.

1 Drawing Figure

BACKGROUND OF THE NEW PLANT

The present invention comprises a new and distinct cultivar of chrysanthemum plant which is a sport of the unpatented off-white chrysanthemum known as Horim. The new cultivar was discovered by Nicolaas Middelburg on Mar. 23, 1975, at 's Gravenzande, in the Netherlands and has been asexually reproduced by cuttings at the same location. The new cultivar has been found to retain its distinctive characteristics through successive propagations.

DESCRIPTION OF THE DRAWING

The accompanying drawing shows the unique characteristics of the new cultivar, the color being as nearly true as possible with color illustrations of this type. The photo shows the new cultivar in various stages of bloom.

DESCRIPTION OF THE NEW PLANT

The new cultivar is a short day response plant and, when grown in the vicinity of 's Gravenzande, Holland, has a response time of about 12 weeks. The new cultivar may be grown year round under greenhouse conditions.

In the description which follows, color references are made to the "Horticultural Colour Chart II" issued by the British Colour Council in collaboration with the Royal Horticultural Society. The following data is based on observations of the new cultivar at 's Gravenzande, Holland. Where meaningful, comparisons are made between the new cultivar, White Horim, and the parent cultivar, Horim.

Petals:

*Texture.*—Thick.
*Appearance.*—Satiny.
*Arrangement.*—Imbricated.
*Persistence.*—Drop off cleanly.
*Fragrance.*—Slight, typical chrysanthemum.

Reproductive organs:

*Stamen, anthers.*—Few, small.
*Pollen.*—Cadmium Orange 8/1.
*Arrangement.*—Tucked inside calyx.

Botanical classification: *Chrysanthemum mortifolium.*

| | White Horim | Horim |
|---|---|---|
| Bloom: | | |
| Size | medium | medium-small |
| Fully expanded | 7–8 centimeters | 6–7 centimeters |
| Borme | several together | several together |
| Stems | medium, strong | medium, strong |
| Form | single (daisy) | single (daisy) |
| Permanence | excellent, 4 weeks | excellent, 4 weeks |
| Color: | | |
| Center of flower | Cyprus Green 59/1 | Cyprus Green 59/1 |
| Base of petals | Agatha Green 60 | Agatha Green 60 |
| Inside of petals | white | white |
| Reverse of petals | white | Pastel Mauve 433/3 |
| Tonality from a distance | white | mauve |
| Discoloration | none | to white, 1–2 weeks after cutting |

*Styles.*—Columnar. Length — short, thin.
*Stigmas.*—Dresden Yellow 64.
*Ovaries.*—Enclosed in calyx.

Plant:

*Form.*—Herbaceous.
*Growth.*—Vigorous.
*Height.*—Medium, depends on culture.

Foliage:

*Top side.*—Scheeles Green 60.
*Size.*—Medium.
*Quantity.*—Normal.
*Shape.*—Pointed oval.
*Texture.*—Velvety.
*Ribs and veins.*—Ordinary.
*Edge.*—Serrated.
*Serration.*—Single, large.
*Underside.*—Scheeles Green 60/2.

I claim:

1. A new and distinct cultivar of chrysanthemum, substantially as described and pictured herein, characterized by its satiny pure white blooms, vigorous growth, 12 week response and permanence, and by having larger bloom and a purer white color than the parent cultivar, Horim.

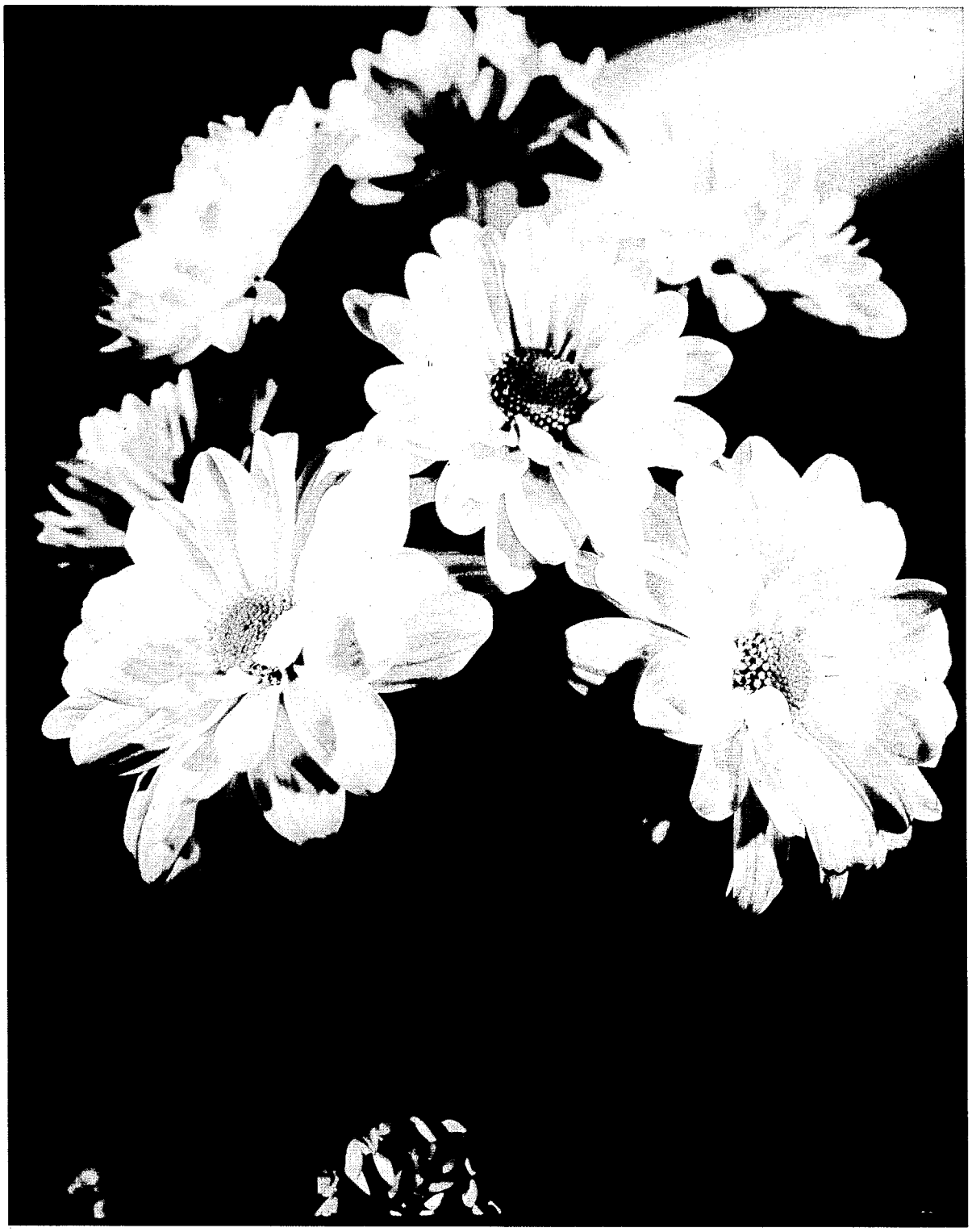

* * * * *